US005674750A

United States Patent [19]
Kraus et al.

[11] Patent Number: 5,674,750
[45] Date of Patent: Oct. 7, 1997

[54] CONTINUOUS SELECTIVE CLONOGENIC EXPANSION OF RELATIVELY UNDIFFERENTIATED CELLS

[75] Inventors: Morey Kraus; Jill Friberg, both of Worcester, Mass.

[73] Assignee: t. Breeders, Worcester, Mass.

[21] Appl. No.: 446,165

[22] Filed: May 19, 1995

[51] Int. Cl.$^6$ .............................. C12N 5/02; C12N 5/08; C07K 16/28
[52] U.S. Cl. ................ 435/372; 435/366; 435/374; 435/376; 435/377; 435/395; 435/403; 503/387.1
[58] Field of Search .................. 435/240.2, 240.21, 435/240.23, 240.24, 240.243, 366, 372, 374, 376, 377, 383, 384, 395, 403; 530/387.1

[56] References Cited

U.S. PATENT DOCUMENTS

| | | | |
|---|---|---|---|
| 4,514,499 | 4/1985 | Noll | 435/240 |
| 5,004,681 | 4/1991 | Boyse et al. | 435/2 |
| 5,061,620 | 10/1991 | Tsukamoto et al. | 435/7.21 |
| 5,399,493 | 3/1995 | Emerson et al. | 435/172.3 |
| 5,460,964 | 10/1995 | McGlave et al. | 435/240.21 |
| 5,472,867 | 12/1995 | Kanz et al. | 435/240.25 |

OTHER PUBLICATIONS

Johnstone et al. Immunochemistry in Practice, 2nd edition, Blackwell Scientific Publications, Osney Mead, Oxford OX2OEL pp. 242–243.

Mayani et al. (1993) Blood. vol. 81(12) : 3252–3258.

*Primary Examiner*—Christina Y. Chan
*Assistant Examiner*—Emma Cech
*Attorney, Agent, or Firm*—Fish & Richardson P.C.

[57] ABSTRACT

A system is provided for selective clonogenic expansion of relatively undifferentiated cells, including (a) a tube containing a plurality of beads of a size which permits a plurality of the undifferentiated cells to grow thereon, the beads bearing on their surfaces a selective binding molecule which binds to a surface antigen present on the relatively undifferentiated cells, wherein the antigen is not present on the surfaces of the relatively differentiated cells; (b) means for continuously providing nutrients to the relatively undifferentiated cells growing on the beads, wherein the nutrients are delivered via a fluid which flows through the tube and past the beads; and (c) means for continuously harvesting the relatively undifferentiated cells downstream of the beads.

26 Claims, 5 Drawing Sheets

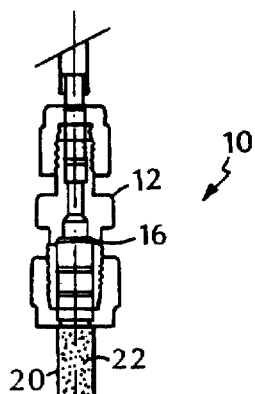
FIG. 1
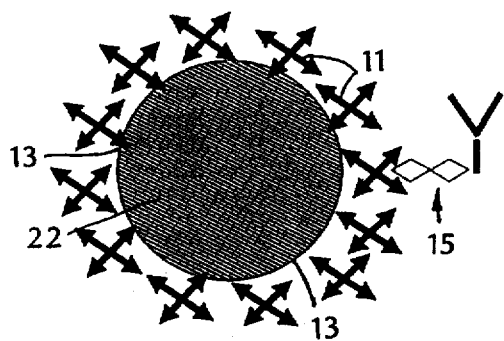
FIG. 1A
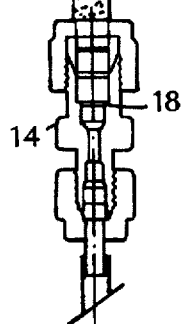
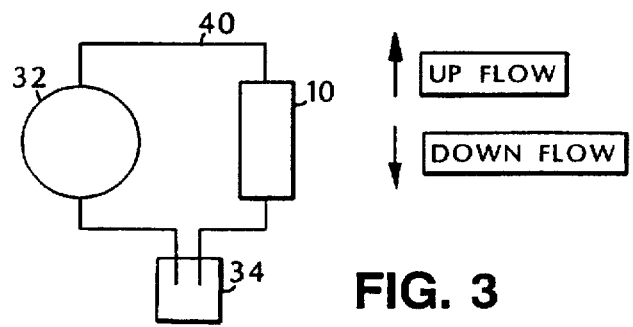
FIG. 2
FIG. 3
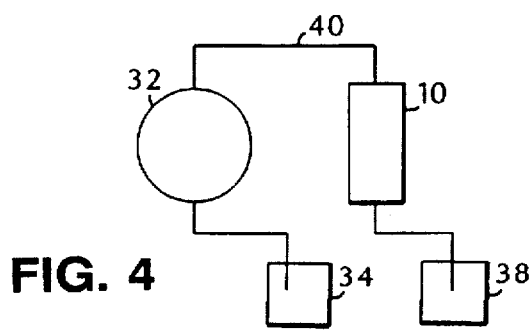
FIG. 4

CONTINUOUS SELECTIVE CLONOGENIC EXPANSION OF RELATIVELY UNDIFFERENTIATED CELLS

BACKGROUND OF THE INVENTION

This invention relates to systems for clonogenic expansion of relatively undifferentiated cells.

The origin of all the cells in blood and in the immune system is the hematopoietic stem cell (HSC). Each HSC has the potential to differentiate into at least eight separate blood cell lineages within the myeloid and lymphoid blood cell compartments. It has been estimated through successive generational analysis that one HSC has the potential to produce up to fifty million differentiated progeny. See U.S. Pat. No. 5,061,620, the disclosure of which is incorporated herein by reference in its entirety.

This enormous potential could be exploited if, starting from a small number of HSCs, a large pool of HSCs could be bred in isolation without differentiation or mixed culture expansion. This pool of HSCs could then be used to restore or supplement an immune system and/or blood forming system compromised by, e.g., radiation or chemotherapy, and as a valuable tool in the design, development and testing of diagnostic and therapeutic agents used in the treatment of immune system and/or blood forming disorders.

Efforts have been made to develop a system which would grow HSCs ex vivo and control cell proliferation and differentiation. Typically, these efforts have involved batch culture of a mixed population of cells which have been initially separated from a large volume of blood.

SUMMARY OF THE INVENTION

The invention is based on our discovery that cells, in particular renewable cells, e.g., relatively undifferentiated cells including HSCs, can be clonogenically expanded in a continuous (as opposed to batch) process using a continuous perfusion bioreactor.

Accordingly, in one aspect, the invention features a method of continuous selective clonogenic expansion of a predetermined population of cells, including the steps of: (a) providing a chamber having an inlet, an outlet, and a passage for fluid flow from the inlet to the outlet, and, disposed in the chamber, a solid support (i.e., a matrix such as polymer beads) capable of supporting a plurality of living cells adhered thereto, wherein the support includes a plurality of selective binding molecules with specific affinity for the predetermined population of cells; (b) causing fluid containing a plurality of cells of the cell population to flow through the chamber, so that a portion of the cells bind to the binding sites; (c) causing fluid containing nutrients to flow through the chamber to cause the bound cells to divide; and (d) continuously harvesting cells of the predetermined population as they exit the chamber with the fluid.

In preferred embodiments, the solid support includes a plurality of beads disposed in the chamber in a packed configuration, preferably having a size which allows both cells not of the predetermined population and dividing cells to pass through spaces in the packed configuration. The specific affinity is preferably provided by a selective binding molecule that binds to a cell surface antigen on cells of the predetermined cell population but not on cells not in the cell population. Preferably, the selective binding molecule is selected to retain the bound cells sufficiently strongly so that they are not washed off by flow of the nutrient-containing fluid and thus reseeding of the chamber with cells after the initial seeding has been carried out is not necessary. In one preferred embodiment, the surface antigen on the relatively undifferentiated cells is CD34, and the selective binding molecule includes a biotinylated antibody, e.g., biotinylated CD34, for binding the CD34. It is also preferred that the selective binding molecule be bound to the surface binding site by a coupling agent selected to bind the selective binding molecule in an advantageous stereospecific orientation. Preferred coupling agents include avidin derivatives. To reduce non-specific interaction, it is preferred that, prior to step (d), plasma, or another agent capable of preventing non-specific interactions, be caused to flow through the chamber to allow a portion of the plasma to bind to regions of the solid support on which selective binding molecules are not present. The plasma may be autologous or type-matched allogeneic plasma. It is also generally preferred that the fluid via which nutrients are delivered flows at a rate which ensures that the oxygen saturation of the fluid flowing though the matrix is not greater than 20% at the inlet while remaining greater than 0% at the outlet, relative to the solubility of oxygen in the fluid at equilibrium with air at 37° C. and 1 atm pressure. This oxygen content is provided in preferred systems by flow rates of from about 0.1 ml/hr. to 8 ml/hr., more preferably from about 0.5 to 1.5 ml/hr.

One system of the invention for continuous selective clonogenic expansion of relatively undifferentiated cells including: (a) a tube containing a plurality of beads of a size which permits a plurality of the undifferentiated cells to grow thereon, the beads bearing on their surfaces a plurality of selective binding molecules capable of binding to a surface antigen present on the relatively undifferentiated cells, wherein the surface antigen is not present on relatively differentiated cells; (b) means for continuously providing nutrients to the relatively undifferentiated cells growing on the beads, wherein the nutrients are delivered via a fluid which flows through the tube and past the beads so that the relatively undifferentiated cells in the tube divide and at least a portion of relatively undifferentiated cells exit the tube with the fluid; and (c) means for continuously harvesting the portion of the relatively undifferentiated cells that exit the tube.

The invention can be used to provide stem cells (HSCs) useful for enhancing the immune response of a patient. The patient's blood or bone marrow is withdrawn (or an allogeneic stem-cell containing sample is provided); stem cells are expanded and harvested according to the invention; and then those cells are re-introduced into the patient, where they will facilitate reconstitution of the patient's immune and/or blood forming system.

Preferably, the sample taken from the patient is relatively small, e.g., less than about 100 to 200 ml, to minimize trauma to the patient. The preferred potency and dosage of the undifferentiated cells to administer to the patient, and duration of administration, will vary depending upon the condition of the patient's immune or blood forming system, but would generally be expected to be in the range of from about 100 to $1 \times 10^6$ cells/dose/day.

Alternatively, the invention can be used to provide to a patient a predetermined population of relatively differentiated cells, by providing a sample containing a population of cells which cells are the progenitor to the predetermined population, and using the system of the invention to bind the progenitor cells and cause the bound cells to proliferate and differentiate to form the predetermined population of cells, e.g., by providing the cells with a growth factor which will cause differentiation. For example, the differentiated cells may be lymphoid precursors, myeloid precursors or erythroid precursors. The invention can also be used to provide to a patient a therapeutic compound produced by a population of cells, e.g., a humoral factor, by using the system of the invention to bind cells of the population and to cause the population to produce the substance.

The invention also features a method of inducing proliferation of a population of relatively undifferentiated cells including contacting the cells with a nutrient media that is free of growth factors.

The invention further features a method of reducing negative feedback during selective clonogenic expansion of relatively undifferentiated cells including immobilizing a population of relatively undifferentiated cells on a solid support, providing a nutrient-containing fluid to the cells, continuously removing waste products and by-products of the cells from contact with the immobilized, relatively undifferentiated cells, while continuously removing proliferating cells immediately after they are formed.

The invention also features a cell population including greater than 60% of relatively undifferentiated cells having a diameter of from 3 μm to 12 μm. This, cell population, which was previously unknown, was first identified by means of the bioreactor of the invention. It is believed that this population of cells is a highly pluripotent, medically useful population.

Advantageously, the continuous harvesting of the invention allows samples of undifferentiated cells to be obtained in which a majority of the cells exiting the bioreactor at any given time are synchronous in both cell cycle and age by virtue of having recently undergone cell division.

The invention further features a method of making a bioreactor for the expansion and harvesting of a predetermined population of cells, the method including: (a) providing a chamber having an inlet, an outlet, and a passage for fluid flow from the inlet to the outlet, and, disposed in the chamber, a solid support capable of supporting a plurality of living cells adhered thereto, wherein the support includes a plurality of binding sites with specific affinity for the predetermined population of cells; (b) causing fluid containing a plurality of cells of the cell population to flow through the chamber, so that a portion of the cells bind to the binding sites; and (c) freezing the chamber to preserve the cells in a potentially viable state. The method can also include thawing the chamber, causing fluid containing nutrients to flow through the chamber to cause the bound cells to divide; and continuously harvesting cells of the predetermined population as they exit the chamber with the fluid.

In yet another aspect, the invention features a cell population including greater than 80% CD34+ cells: such a population was not possible prior to the invention. In preferred embodiments, the population includes greater than 90% CD34+ cells, more than 80% of which are viable, i.e., the number of live cells divided by the total number of cells equals 80% or greater. Preferably, the majority of the population tests negative for CD38, CD33, CD19 and HLA-Dr, which are antigens defining relatively differentiated cells.

The invention further features a cell population that includes a series of samples of undifferentiated cells, each of which was harvested during a different time interval, all of the time intervals having the same length. The inventors have found that these samples, if the time intervals and cell counts are measured accurately and the bioreactor process parameters are maintained constant, will each contain substantially the same number of cells.

The term "continuous", as used herein, refers to a process which proceeds substantially constantly, with dividing cells being removed from the bioreactor shortly after they are born, rather than remaining in culture as in a conventional batch process. This term, as used herein, does not imply that the process is necessarily a steady-state process, although in some preferred embodiments steady state may potentially be reached.

Thus, the invention provides tremendous potential for continuous long-term production of cell populations which, advantageously, can be supplied to a patient or other user of the cells almost as soon as the cells are born (or frozen as soon as they are harvested and supplied in frozen form at any desired time). As a result, the populations tend to be synchronous in both cell cycle and age, resulting in superior predictability when the cells are used for treatment or diagnostics. The internal synchronization of growth rates of the cells attached to the matrix attributable to continuous culture kinetics (D=μ) (see Principles of Fermentation Technology, P. F. Stanbury & Whitaker, Pergammon Press 1st ed 1984 Oxford, England p. 14), enables the bioreactor to be used as a research tool for studying the effects of biopharmacological agents, growth factors, mitogens and the like.

Moreover, because dividing cells are continuously harvested from the column almost as soon as they are formed, the feedback from cell waste and cell by-products which plagues batch systems is virtually eliminated, allowing an extremely pure cell population to be harvested.

The invention can be used not only to proliferate relatively undifferentiated cells, but also to produce populations of other cells simply by selecting the appropriate growth factor to supply to the bioreactor during expansion, and to produce desired cell by-products, e.g., those which could be administered as therapeutic compounds to a patient. Because the initial cell sample can be autologous, the cell populations or cell by-products produced are likely to be readily accepted by the patient from whom the cell sample was obtained.

Because the entire bioreactor can be frozen, a sample can be taken from a patient, charged to the bioreactor, and then saved for a prolonged period for later use when needed, e.g., when the patient's immune system or blood forming system is challenged.

Moreover, because cells harvested from one bioreactor can be used to "seed" a second bioreactor, e.g., if the first bioreactor is reaching the end of its useful life, expansion can proceed virtually indefinitely from a single small cell sample. Also, the cells harvested from one bioreactor can be used to seed a second bioreactor that could in turn be used to expand a desired cell population or produce a desired by product.

Other features and advantages of the invention will be apparent from the following detailed description, and from the claims.

DETAILED DESCRIPTION

The drawings will first be briefly described.

DRAWINGS

FIG. 1 is a somewhat schematic cross-sectional side view of a bioreactor of the invention.

FIG. 1a is a highly enlarged, diagrammatic view of a bead used in the bioreactor of FIG. 1.

FIG. 2 is a schematic diagram showing the bioreactor in use for cell proliferation.

FIG. 3 is a schematic diagram showing the bioreactor during initial cycling with reagent.

FIG. 4 is a schematic diagram showing the bioreactor during a rinse cycle subsequent to cycling with reagent.

THE BIOREACTOR

Figure 5:
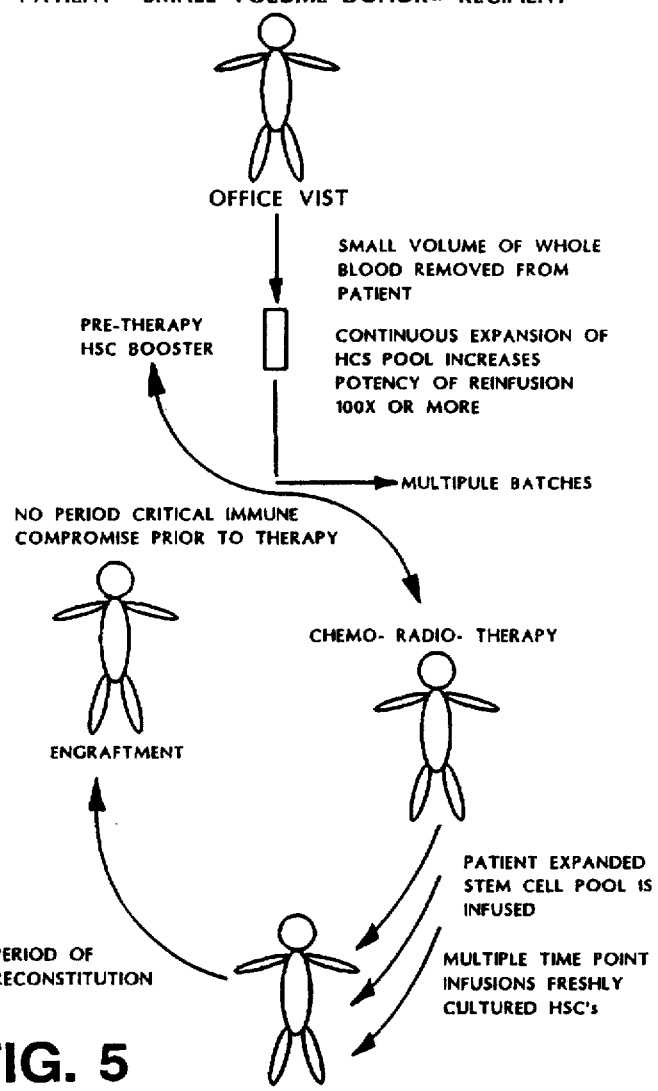
FIG. 5 is a schematic flowchart showing a method, according to one embodiment of the invention, of treating a patient with HSCs proliferated as shown in FIG. 2.

Referring to FIG. 1, bioreactor 10 includes two reducing union connectors 12, 14, mesh grids 16, 18 disposed in the orifice of each reducing union, and a culture column 20, disposed between the two mesh grids 16, 18, containing surface activated beads 22. Mesh grids 16, 18 retain the beads in the culture column 20.

Prior to use of the bioreactor, a coupling agent 11 is bound to the activated sites 13 at the surface of the bead 22, and a selective binding molecule 15, selected to bind a surface antigen present on relatively undifferentiated cells but not on relatively differentiated cells, is in turn bound to the coupling agent 11, forming the surface layer shown schematically in FIG. 1a. The coupling agent is provided between the selective binding molecule and the activated site in order to control the stereospecific orientation in which the selective binding molecule extends from the bead surface. It has been found that, by providing the coupling agent, more desirable orientations can be obtained. However, if desired, the selective binding molecule 15 can be bound directly to the surface of the bead, if the orientation of the selective binding molecule is not a concern, e.g., if enough activation sites are provided that a sufficient number of molecules will have an orientation which will bind the relatively undifferentiated cells.

The manner in which the coupling agent and selective binding molecule are bound to the beads during manufacture of the culture column, to form the structure shown in FIG. 1a, is described in detail in the "Bioreactor Setup" and "Examples" sections below.

Bioreactor Set-Up

Before cell proliferation, described in the "Bioreactor Use" section, below, can begin, it is necessary to prepare the bioreactor by binding the coupling agent and selective binding molecule to the surface of the beads in the bioreactor, to form the bead surface shown diagrammatically in FIG. 1a (i.e., to prepare the beads to bind the cells to be proliferated).

The coupling agent is applied by recycling a solution of the coupling agent through the bioreactor while the bioreactor is connected in the configuration shown in FIG. 3 (a cycling configuration). After the coupling agent has been cycled through the bioreactor for sufficient time to cause the coupling agent to bind to substantially all of the activated sites on the beads (see, for example, the procedure described in Example 1, below), the column is rinsed, as shown in FIG. 4, to remove excess coupling agent which is not strongly bound to the beads. The selective binding molecule is then applied in the same manner as the coupling agent (see FIG. 3) and the column is again rinsed (see FIG. 4).

After the coupling agent and selective binding molecule have been applied to the beads, a plasma or plasma solution, preferably autologous or blood type cross-matched plasma, is applied in a similar manner. Preferably, the plasma is cycled through the bioreactor for about 4–6 hours. It is believed that a component of the plasma functions to coat any areas of the beads which are not coated with the other reagents, thus preventing non-specific interaction between the beads and undesirable cell populations. The effect of the plasma on non-specific interaction is shown graphically in FIG. 6. Other reagents can be used instead of plasma, provided that they bind to the bead surface, do not promote cell differentiation, and do not promote nonspecific interaction.

Preferably, substantially all of the plasma (except for the small portion that is apparently bound to the beads) is rinsed from the column prior to use. Generally, it is preferred that no unbound plasma be present in the bioreactor during cell proliferation, as this unbound plasma could cause cell differentiation. However, if non-specific interaction increases in the bioreactor during use due to washing off of the plasma coating, it may be desirable to introduce a small amount of plasma, or a reagent which would function in a similar manner, to the bioreactor during use to prolong the life of the column.

During the bioreactor set-up steps described above, the incubator is preferably maintained at the same conditions described above for the cell proliferation process.

Bioreactor Use

To use the bioreactor described above for stem cell expansion and harvesting, the bioreactor 10 is placed in a cell proliferation system 30, shown schematically in FIG. 2, which includes a peristaltic pump 32 to provide flow of fluid through the system, a reagent reservoir 34, a sampler tube 36, a waste reservoir 38, and tubing 40 connecting these components in the illustrated arrangement. The cell proliferation system 30 is disposed within an incubator 31 (e.g., an incubator commercially available under the tradename NuAire NU-2700) which is maintained at approximately 37±2 degrees C, 85–90% RH and 5% $CO_2$ in air throughout the cell proliferation process.

To use the bioreactor system, a sample containing CD34+ cells, e.g., Ficoll-Paque Gradient Purified Mononuclear Fraction (MNF) (approx. $5 \times 10^7$ mononuclear cells/ml.) from peripheral or cord blood, preferably a sample of a patient's own blood, is fed to the bioreactor through feed line 40a. Preferably, the peristaltic pump is operated at approximately 0.89 ml./hr. during feed of the sample to the bioreactor. The reactor should be prevented from running dry during feeding by backfilling the sample tube with a rinse solution, e.g., Iscoves Modified Dulbecco's Medium (IMDM). The pump should be run for a period sufficient to completely feed the MNF and thus saturate the activated sites on the beads with CD34 cells (or, if a sample is used which contains too few CD34 cells to entirely saturate the activated sites, to bind substantially all of the CD34 cells in the sample to activated sites, after which cells resulting from cell proliferation will bind to the remaining sites). For a sample size of 1 ml. containing approximately $5 \times 10^7$ cells, this will typically take about 3 hours.

Once the sample has been fed through the bioreactor as described in the preceding paragraph, the pump is temporarily shut off while the feed line 40a is connected to reagent reservoir 34 containing a nutrient media solution, preferably Iscove's Modified Dulbecco's Medium (IMDM), commercially available from, e.g., GIBCO BRL Products. Other nutrient media can be used; preferably the media is a defined nutrient media which is substantially free of components which could cause cell differentiation in the bioreactor, e.g., sera or growth factors. It may, of course, be desirable to add growth factors and/or sera under certain circumstances, e.g., where it is desired to predispose the HSCs to differentiate into a particular progeny, as discussed below in the Reagents section.

The pump is then restarted, again preferably at approximately 0.89 ml/hr, and cell proliferation is allowed to proceed continuously while the nutrient media is fed through the bioreactor.

As soon as substantially all of the activated sites on the beads are saturated, dividing cells will begin to flow out of the column with the exiting media, to be harvested in the sampler tube (or any other suitable reservoir or conduit). This continuous cell harvesting will proceed, absent mechanical failure or contamination, for the life of the column, e.g., until the reagents in the bioreactor are depleted through column erosion.

Process Parameters

A number of parameters can be varied to affect the rate and purity of the cell output obtained during bioreactor use.

For example, the flow rate and dilution rate of the nutrient media flowing through the bioreactor during cell proliferation can be varied over a fairly broad range. Generally, it is important that the flow rate be sufficient to provide adequate oxygen to the cells, yet not so high as to wash the reagents and/or bound cells off of the beads. To optimize the volume of cell output obtained, it is preferred that the dilution rate be as high as possible without causing bound cells to be washed from the column. The relationship between dilution rate and cell concentration is described in Principles of Fermentation Technology, P. F. Stanbury & A. Whitaker, Pergammon Press, New York, 1984, at pp. 14–17.

The dimensions of the bioreactor can also be varied. The relationship between bioreactor length and width (the aspect ratio) can be varied to maximize control of process parameters.

The volume and purity of the initial sample fed into the column could also be varied. A smaller volume and higher purity would tend to produce a harvest having a greater percentage of highly positive CD34 cells.

Reagents

Coupling agents

Suitable coupling agents for binding the selective binding molecule to the bead surface are those agents which will bind the desired selective binding molecule, but will not bind undesired compounds. When the selective binding molecule is a biotinylated antibody, preferred coupling agents include avidin, streptavidin, NeutrAvidin (commercially available from Pierce Chemical, Rockford, Ill.), and other avidin derivatives. NeutrAvidin is preferred because its pI (isoelectric point) is substantially neutral and thus this protein exhibits very low non-specific binding.

Selective binding molecules

Preferred selective binding molecules are biotinylated antibodies. Other suitable selective binding molecules include cell adhesion molecules, a mix of lineage specific antigen receptors, or, if no coupling agent is used, a non-biotinylated antibody (biotinylation is only necessary in order to effect binding of the antibody to the coupling agent).

Reagents which are suitable for biotinylation of the antibody include NHS-biotin, biotin hydrazide, biotin BMCC, and other biotin derivatives. NHS-biotin is preferred, as it appears to have minimal effect on the reactivity of the antibody. Processes for biotinylation are well known. An example of a suitable process is given below in the Examples section.

Suitable antibodies include monoclonal CD34 epitopes and polyclonal CD34 or any uniquely identifiable cell surface antigen or binding site for a desired cell population. Mixtures of antibodies can also be used to enhance antibody/cell interactions, both in number and strength of the interactions, which can allow higher flow rates to be used without cells washing off of the beads.

Other reagents

A suitable rinse solution to rinse the culture column both after application of the coupling solution and after application of the biotinylated antibody is Dulbecco's PBS, pH 7.4. A suitable rinse solution to rinse the column after application of the plasma is Iscoves Modified Dulbecco's Medium (IMDM), which is also used as the nutrient media to promote cell proliferation. Other suitable rinse solutions and nutrient media are known to those skilled in the art. Preferably, when the bioreactor is being used to expand relatively undifferentiated cells, the nutrient media is serum-free and free of growth factors, to prevent possible serum or growth factor induced differentiation. However, it may be desired in some cases to include serum and/or growth factors, e.g., when it is desired to produce a differentiated population from the bound cells. It may also be desirable for the nutrient media to be conditioned by cell growth to contain proteinaceous growth factors. The level of these growth factors in the media can be enhanced by recycling the nutrient media through the chamber while concurrently removing dividing cells from the chamber.

Bioreactor Materials

The reactor components (culture column, tubing, fittings, etc.) should be autoclavable, and preferably also able to withstand gamma irradiation and other harsh methods of sterilization. Moreover, the reactor components should be compatible with tissue culture and should not leach undesirable compounds into the culture medium. The reactor parts further should not accommodate or promote adherence of cells, e.g., by lineage specific antigen receptors, cell adhesion molecules (CAMs) on the cell surface, or secretion products of the cultured cells, unless such antigens, CAMs or secretion products are specifically incorporated into the selection criteria for a given cell proliferation process.

Suitable materials which meet these criteria include polypropylene, stainless steel, polytetrafluoroethylene (TEFLON), PFA, and other inert medical grade materials well known in the art. For the tubing, silicone may in some cases be preferred for its relatively high oxygen permeability (allowing sufficient oxygen to reach the cells at lower flow rates); in other cases polytetrafluoroethylene may be preferred for its very low non-specific interaction potential.

The fittings which connect the bioreactor to other elements of the system should be able to accommodate low holdup volume, withstand minimal pressures (typically less than 10 psi), and allow for minimal constriction of flow so as to reduce channeling and adverse fluid flow patterns which might result in inadequate wetting of the column core.

erosion of surface coatings on particles, or disruption of cells attached to the beads.

The beads are preferably borosilicate glass beads having epoxide groups at their surface. Such beads are commercially available from, e.g., Potters Industries, Inc., Parsippany, N.J., under the tradename Glass Spheres A and P series.

Other bead materials, e.g., polystyrene, or surface activations, e.g., carboxyl, can be used, provided that the surface of the bead is non-porous, to avoid trapping cells or other material in pores on the bead surface, and sufficiently smooth to allow cells, compounds and particulate matter in the chamber to flow past the surface without adhering thereto or diffusing therein. The surface activation can be in the form of reactive groups extending from the surface of the bead due to the structure of the bead material or the manner in which the surface has been chemically treated, or can be in the form of a reactive group extending from a coating applied to the bead surface. For example, the bead could be a polypropylene or other polymer bead and the surface activation could be a crosslinked coating, e.g., of an amino acid. The reactive group is selected to be capable of binding the selected coupling agent or, if no coupling agent is used, binding the selective binding molecule itself. Preferably, the surface activation includes a sufficient number and type of binding sites to allow the beads to bind 8–12 μg NeutrAvidin per gram of beads at pH 5.0 (0.1M phosphate buffer) at room temperature during a 12–16 hour cycling process (e.g., the process shown in FIG. 3). The number of binding sites can be varied, however, to suit particular column dimensions, flow rates, or other process parameters. The bond formed with the reactive group (by the coupling agent or by the selective binding molecule, if no coupling agent is used) is typically covalent.

Preferably, the beads have a diameter of about 250–550 more preferably 350–450 μm. Smaller beads, when packed in the column, may not be sufficiently far apart to allow flow of cells through the column, while larger beads may not provide sufficient available surface area to enable efficient cell interaction. The size and size distribution of the beads can be varied, however, to vary the surface area or number of binding cites available for a column having given dimensions.

In some cases, it may be desirable to include a spacer zone of non-activated beads at the top, bottom, or a specific region of the column, or mixed with the activated beads. Such a spacer zone could be used to diffuse flow so that high flow rates within the column are prevented from washing the reagent coating off of the activated beads.

Therapeutic Use

As shown schematically in FIG. 5, a patient requiring immunotherapy would first have a small volume of his or her blood drawn. This blood would then be used as described above (Bioreactor Use section) to produce a pool of autologous HSCs, which would be administered to the patient as an immune system booster prior to a treatment damaging the patient's immune system and/or blood forming system (e.g., chemotherapy), and/or as a stimulant to the patient's compromised immune or blood forming system after the treatment.

Alternatively, a cell sample could be used to produce a pool of a selected population of differentiated cells, by charging the cells to a bioreactor of the invention and supplying to the bioreactor one or more growth factors selected to cause the cells to differentiate to cells of the selected population. The use of growth factors for selective expansion of cell populations is discussed in, e.g., WO 93/08268.

EXAMPLES

Example 1

CD34 HPCA-2 (Human Progenitor Cell Antigen 2) was biotinylated with NHS-Biotin using the following procedure:

Dialyzed 1 ml. of a 25 ug/ml stock solution of antibody against 1500 ml. of a dialysis buffer, e.g., 50 mM bicarbonate buffer pH 8.5, in a Dialyzer Slide (Pierce Chemical, Rockford, Ill.) for 12–16 hours. Immediately before using, dissolved 1 mg of the NHS-biotin in 75 ul DMSO. Added 25 ul of this solution to the dialysate. Incubated at room temperature for 1 hour. Transferred to a Centricon-30 microconcentrator (Amicon) and spun at 14,000 cgf for 12 minutes to remove unreacted biotin. Recovered the retentate in a 1.5 ml Eppendorf tube. Brought the volume up to 1.5 ml with Dulbecco's PBS. Stored in the dark at about 4° C. and used within one day.

A bioreactor, as shown in FIG. 1, was then assembled as follows:

1. Using a standard one-hole paper punch (0.25" punch), made two 0.25" diameter grids from 210 μm polypropylene mesh. Carefully placed the grids into the 0.508 cm orifices of two stainless steel reducing unions. Used 0.508 OD PFA tubing to guide the grid into place at the inner lip of the reducer.

2. Cut a 5 cm length of 0.508 cm OD PFA tubing (PFA-T4-062-100, Cambridge Valve and Fitting) using a razor blade, taking care to make a perpendicular cut so that the tubing would lay flush against the grid in the reducer.

3. Assembled one of the reducing unions onto one end of the length of tubing, using a TEFLON front and back ferrule arrangement.

4. Loaded approximately 0.55 grams (+/– 0.05 grams) of epoxy activated borosilicate glass beads into the bioreactor, making certain that the beads completely filled the tubing, so that no unnecessary voids were present.

5. Installed the other reducing union and front and back ferrule at the other end of the tubing, seated ends and finger tightened.

6. Installed a 2 cm length of 0.318 OD PFA tubing (PFA-T4-062-25, Cambridge Valve and Fitting) and a TEFLON front and back ferrule at each 0.318 ID end of the reducing union. Finger tightened.

7. Installed a 50 cm length of #13 Pharmed tubing (H-06485-13, Cole-Parmer) onto each 0.318 OD PFA tubing, resulting in a closed, autoclavable loop.

8. Hand tightened all fittings. Autoclaved the bioreactor at 121° C. for 30 minutes with a 15 minute dry goods exhaust. Upon removal from the autoclave, transferred the bioreactor to an 80° C. drying oven for about 3 hours to remove residual moisture.

9. Allowed the bioreactor to cool and re-tightened all fittings with a wrench.

10. Placed the bioreactor on a stand and loaded the #13 Pharmed tubing into a peristaltic pump.

Next, the bioreactor was loaded with reagents (Bioreactor Set-Up) as follows:

1. Using scissors, the #13 Pharmed Tubing was cut approximately 5 cm from the lower outlet of the bioreactor.

The unsheathed end of a 1" 21 gauge Vacutainer Collection Needle was inserted into each of the freshly cut ends of the #13 tubing. The sheath was then removed from the other end of the needles and used to puncture the top of a 1.5 ml Eppendorf Microfuge tube containing 1.5 ml of a coupling solution (100 μg NeutrAvidin in pH 5.0 phosphate buffer (0.1M) made and filter sterilized (0.2 μm) immediately prior to use). This procedure results in the system configuration shown in FIG. 3.

2. Started the peristaltic pump at 50% pump output (0.89 ml/hr.) so that the coupling solution was pumped up through the bioreactor, thus reducing the likelihood of air entrapment which could produce adverse channeling effects. After about half the liquid volume had been reduced, added an additional 0.5 ml of the coupling solution to ensure that the bioreactor would be adequately supplied with solution during the entire coupling procedure. Allowed the coupling solution to recycle through the system loop for 16 hours.

3. Stopped the pump and reconfigured as shown in FIG. 4 as follows: Changed pump directional control to allow solution to be pumped down. Broke the recycle loop, being careful not to introduce air, by removing one end from the 1.5 ml Eppendorf tube. Attached this end into a pre-sterilized feed bottle containing a rinse solution (20 ml of Dulbecco's PBS pH 7.4). Primed the feed bottle using a luer lock syringe to apply positive pressure on the sterile exhaust filter. Removed the other end from the Eppendorf tube and installed it onto a pre-sterilized waste bottle.

4. Started the pump at 50% pump output (0.89 ml/hr.) and rinsed the bioreactor with rinse solution for 3 hours.

5. Stopped the pump. Reconfigured as shown in FIG. 3 by transferring the feed and waste lines to the 1.5 ml of NHS-CD34 biotinylated antibody solution prepared above. Started the pump at 50% pump output and ran it in this configuration for 6 hours.

6. Stopped the pump and repeated the reconfiguration and rinse cycle described in step 3 above.

7. Stopped the pump. Reconfigured as shown in FIG. 3, placed a 1.5 ml Eppendorf tube containing 1.5 ml of autologous blood plasma into the recycle loop. Started the pump at 50% output and recycled for 6 hours.

8. Stopped the pump.

The pump was then reconfigured for cell proliferation, i.e., to the configuration shown in FIG. 2. Step 3 was then repeated, replacing the rinse solution with 1 liter of Iscoves Modified Dulbecco's Medium (IMDM).

Cell proliferation then proceeded as follows:

1 ml of fresh Ficoll-Paque Gradient Purified Mononuclear Fraction (MNF) from peripheral blood was resuspended in HBS at approximately $5 \times 10^7$ mononuclear cells/ml. Attached the MNF to the feed line but otherwise remained in the configuration shown in FIG. 2. Started the pump at 50% output. As the MNF was fed into the bioreactor, the cells were kept in suspension to reduce the potential for clotting or clogging. To prevent the pump from running dry, backfilled the Eppendorf with IMDM for several hours. Did not stop the pump for at least 3 hours after starting the MNF through the bioreactor. Stopped the pump and reinstalled the feed line to the IMDM reservoir. Placed the sampler tube as shown in FIG. 2. Restarted the pump at 50% output. Exchanged the sampler tube daily for analysis by hemocytometer, phase and fluorescence microscopy.

Figure 7:
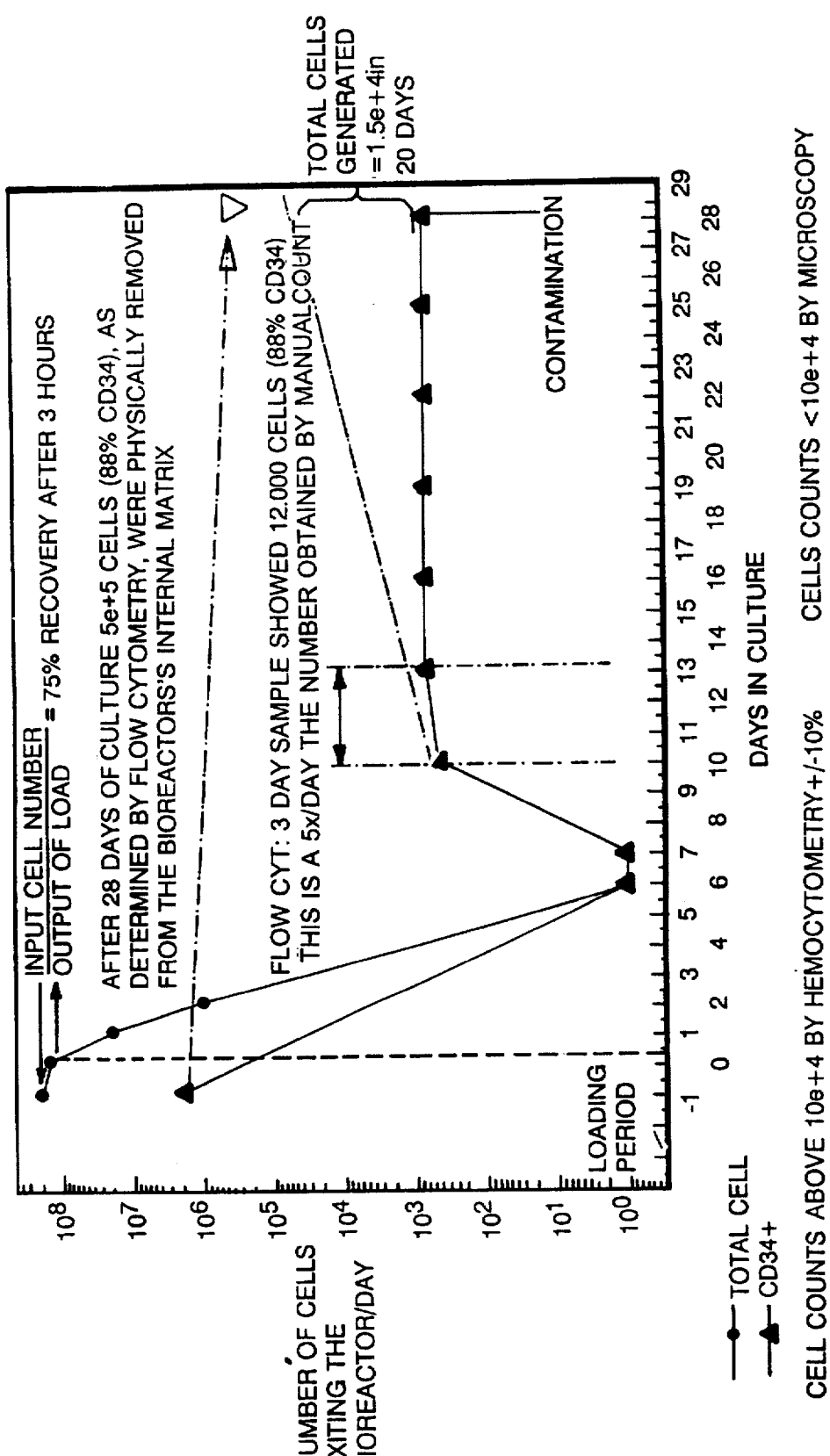
FIGS. 7 and 7a are graphs illustrating, respectively, the results obtained from the experiments described in Examples 1 and 2.

The following results, illustrated graphically in FIG. 7, were obtained from the cell proliferation process using the peripheral blood sample:

MNF passed through the bioreactor=$5 \times 10^7$ mononuclear cells/ml.

MNF recovered in filtrate after 3 hours=$3 \times 10^7$ mononuclear cells/ml. (Note that mononuclear cells continued to appear in the filtrate for 3-5 days after the initial loading. This ended after about 5 days. Included in these fractions were some CD34+ cells which were either loosely bound or large in size, or were in the process of dividing when introduced to the column. Only strongly bound CD34+ population remained in the reactor at 50% pump output.)

During the period from 5 days after inoculation to 8 days after inoculation, substantially no CD34 cells left the bioreactor, indicating that the strongly bound CD34 cells left after the initial 5 day period were remaining on the column and cell proliferation was not yet detectable.

From 8 days after the initial inoculation until bioreactor failure, roughly 100-500 CD34+ cells per day (measured by manual microscopy) appeared in the sampler tube. (The average number of cells collected per day over the life of the column was 350 cells/day. This number is shown in FIG. 7 as the number collected each day, as it appeared that deviation from the average number as merely the result of inaccuracies in the manual counting procedure used.) The harvested cells had a birth diameter of 5+/−2 μm, much smaller than the CD34 cells which were immobilized on the beads in the bioreactor, the diameters of the vast majority of which ranged nominally from about 10 μm to 15 μm. The cell type and relative frequency remained constant for 21 days before the bioreactor succumbed to mechanical failure.

Example 2

The procedures described in Example 1 were repeated, substituting cord blood for the peripheral blood in the cell proliferation process.

Figure 7A:
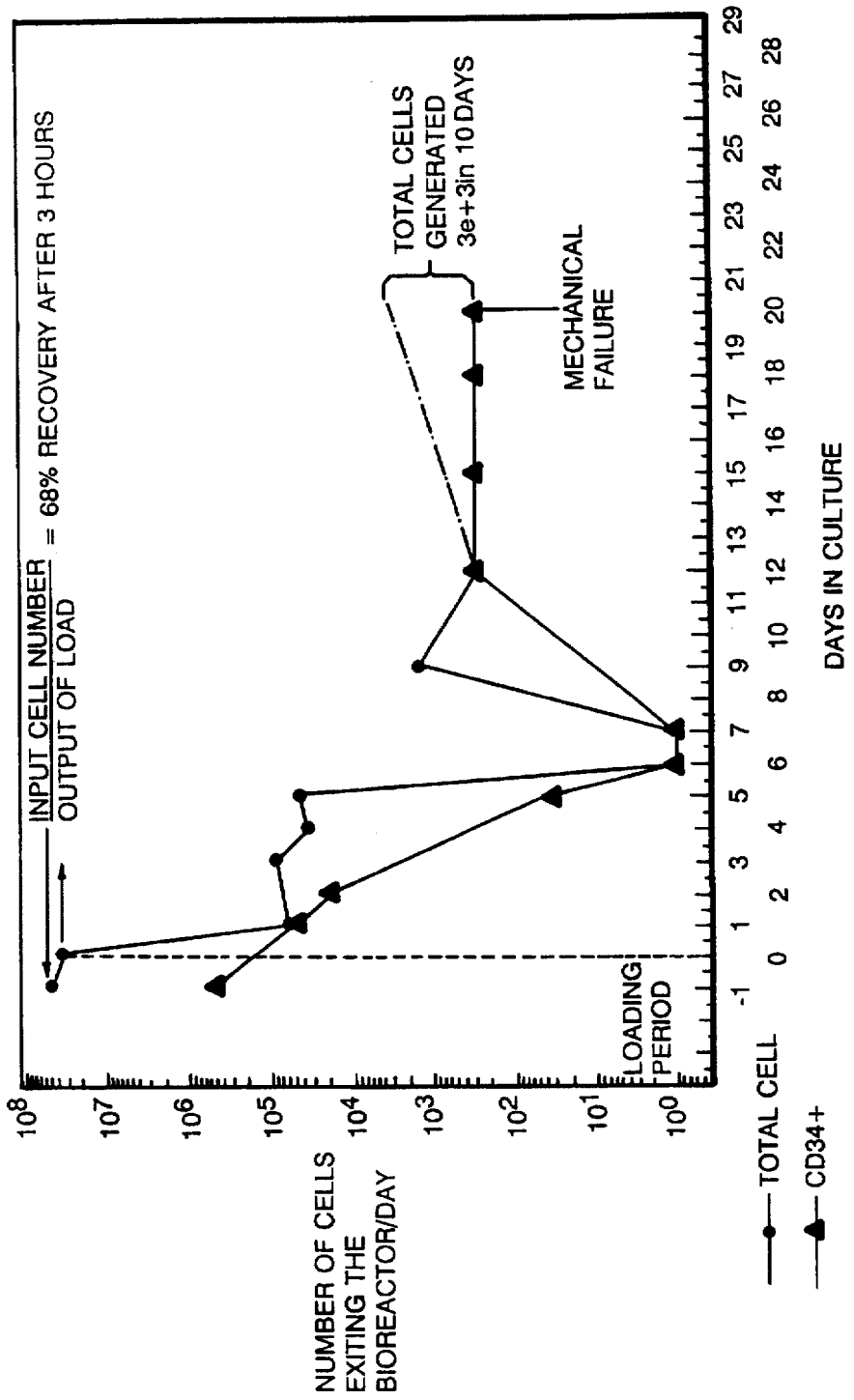

The following results, shown in FIG. 7a, were obtained from the cell proliferation process:

MNF passed through the bioreactor=$5 \times 10^7$ mononuclear cells/ml.

MNF recovered in filtrate after 3 hours=$3 \times 10^7$ mononuclear cells/ml. (As noted above, mononuclear cells continued to appear in the filtrate for 3-5 days after the initial loading.)

From 8 days after the initial inoculation until bioreactor failure, as shown in FIG. 7a, roughly 500-1000 CD34+ cells/day (measured by manual microscopy), with a birth diameter of 5+/−2 μm, appeared in the sampler tube. The average number of cells collected per day was 750, and, for the reasons explained above in Example 1, this is the number that is shown for each day in FIG. 7a. Measured by flow cytometry, a sample taken from the sampler tube for the period between 10 days and 13 days (3 day period) contained 12,000 cells, of which 88% were CD34+ cells. The cell type and relative frequency remained constant for 28 days before the bioreactor succumbed to contamination.

Example 3

Figure 6:
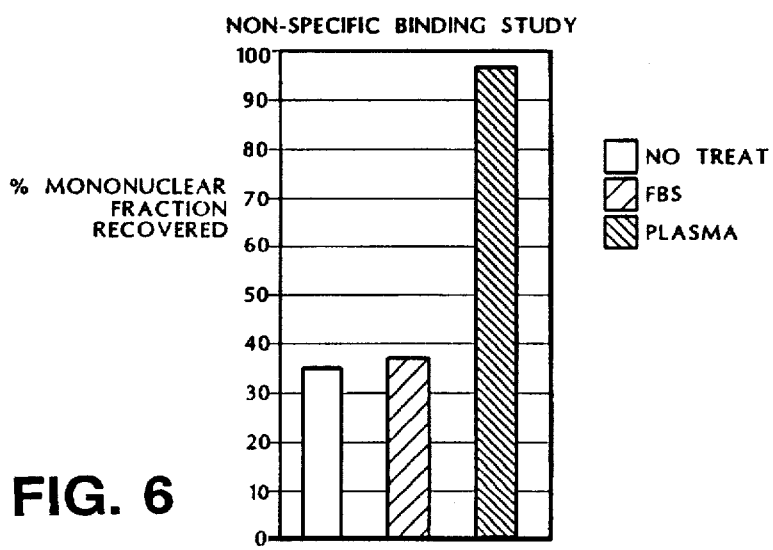
FIG. 6 is a graph illustrating the effect on non-specific interaction of treating the bead surface with, alternatively, plasma or fetal bovine serum.

The effect of treating the bead surface with plasma, or, alternatively, fetal bovine serum, on non-specific interaction at the bead surface was studied. Cord blood was centrifuged under a density gradient (Ficoll-Paque), the mononuclear-fraction (MNF) was removed and concentrated to $1 \times 10^6$ cells in a 10 μl volume. The sample was then injected under flow conditions of 0.89 ml/hr via a septum into a bioreactor which had been prepared as described in Example 1, steps 1-7, using cross-matched human plasma in step 7. This procedure was repeated using a bioreactor which had been prepared as described in the same manner, except that fetal bovine serum (FBS) was substituted for cross-matched human plasma in step 7, and repeated again using a bioreactor which had been prepared as described in Example 1, steps 1-6 (no plasma or FBS treatment). Cells exiting the reactor in each case were counted in a time-wise fashion. The resulting concentration profile was then integrated to obtain the percent of cells recovered. Recovery increases as non-specific interactions decrease, and thus the results of this experiment, shown in FIG. 6, illustrate that non-specific interactions were greatly reduced by treating the bioreactor with plasma, but not significantly reduced by treating the bioreactor with FBS.

OTHER EMBODIMENTS

Other embodiments are within the following claims.

For example, while beads have been described as a preferred matrix material in the Detailed Description above, any material having suitable surface activated sites could be used, provided that the material includes sufficient open space to allow flow of fluid therethrough at sufficient flow rates. Thus, the matrix could comprise a honeycomb, mesh, net, or other material having sufficient surface area and a network of connecting open spaces through which fluid can flow. Alternatively, a fluidized or magnetically stabilized bed could be configured to accomplish similar objectives.

Figure 8:
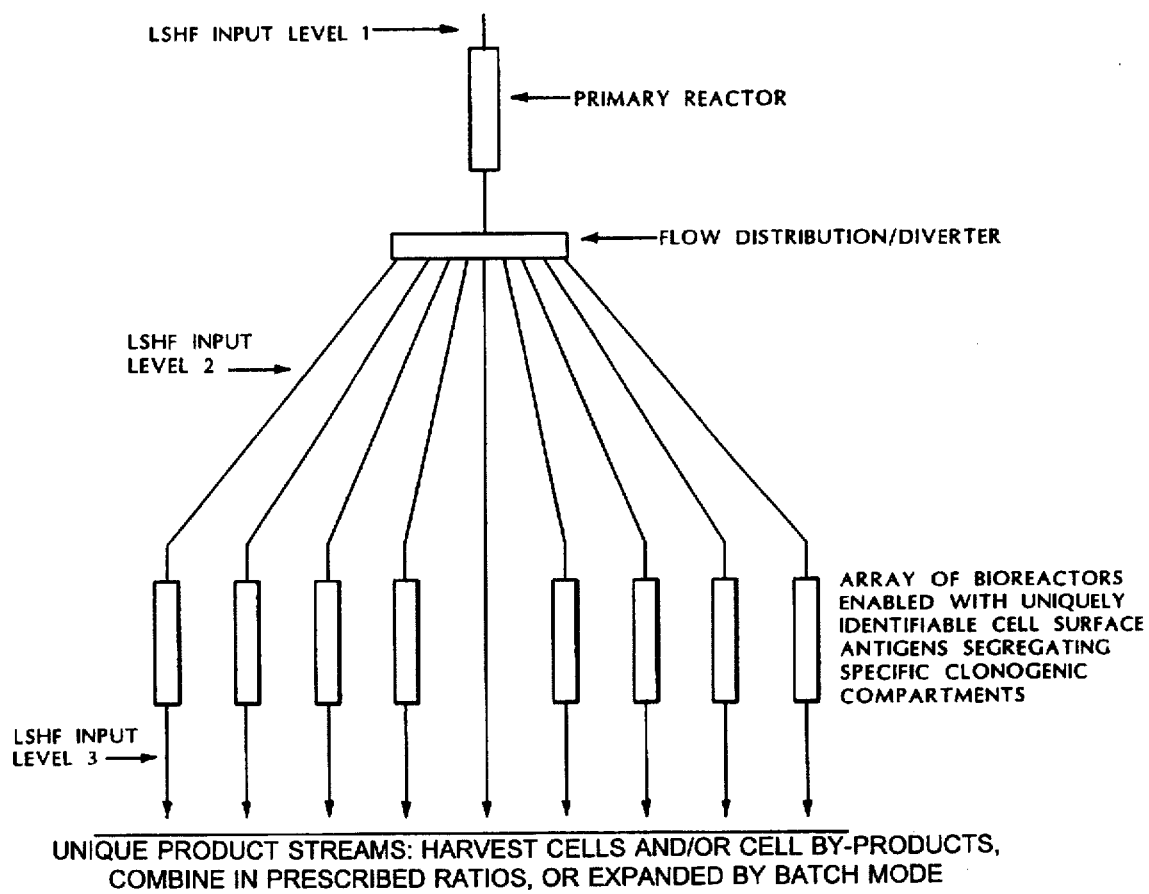
FIG. 8 is a schematic illustration of a plurality of bioreactors of the invention arranged in series to allow the cells harvested from one bioreactor to be expanded, differentiated, or used to produce a cell by-product in another bioreactor downstream therefrom.

Further, while the method of the invention has been described in connection with the expansion of a population of relatively undifferentiated cells, preferably HSCs, the method and system could be used to expand other cell populations. As shown in FIG. 8, relatively differentiated cells could be expanded, e.g., in a bioreactor downstream from a bioreactor used to expand HSCs. While most or all differentiated cells are not renewable, the cells could be expanded for a limited number of generations, or, if the cells are renewable, conceivably for as many expansions as are possible for HSCs.

We claim:

1. A method of selective clonogenic expansion of a predetermined population of cells, said method comprising:
   (a) providing a chamber having an inlet, an outlet, and a passage for fluid flow from the inlet to the outlet, and, disposed in the chamber, a solid support capable of supporting a plurality of living cells adhered thereto, wherein said support comprises a plurality of selective binding molecules with specific affinity for said predetermined population of cells;
   (b) causing fluid containing a plurality of cells of said cell population to flow through said chamber and selecting the flow rate of said fluid through said chamber so that a portion of said cells bind to said binding sites while unwanted cells are removed; and
   (c) causing fluid containing nutrients to flow through said chamber to cause said bound cells to divide.

2. The method of claim 1 wherein said solid support comprises a plurality of beads disposed in the chamber in a packed configuration.

3. The method of claim 2 wherein said beads are sized to allow cells not of said predetermined population to pass through spaces in the packed configuration.

4. The method of claim 2 wherein said beads are sized to allow said dividing cells to pass through spaces in the packed configuration.

5. The method of claim 1 wherein said specific affinity is provided by a selective binding molecule.

6. The method of claim 5 wherein said selective binding molecule is selected to retain said bound cells sufficiently strongly so that they are not washed off by flow of said nutrient-containing fluid and thus reseeding of said chamber with cells after initial seeding has been carried out is not necessary.

7. The method of claim 5 wherein said selective binding molecules are specific for a cell surface antigen present only on cells of said predetermined cell population.

8. The method of claim 7 wherein said selective binding molecule is a biotinylated antibody specific for an antigen on the surfaces of said cells of said predetermined population.

9. The method of claim 5, further comprising the step of causing plasma to flow through said chamber to allow a portion of said plasma to bind to regions of said solid support on which selective binding molecules are not present.

10. The method of claim 9 wherein said plasma is autologous plasma.

11. The method of claim 9 wherein said plasma is a type-matched allogeneic plasma.

12. The method of claim 5, further comprising the step of introducing into the chamber an agent which is capable of binding to regions of said solid support on which said selective binding molecules are not present and preventing non-specific interaction between said regions and materials subsequently introduced into the chamber.

13. The method of claim 1 wherein the surface of said solid support is non-porous.

14. The method of claim 1 wherein the surface of said solid support is sufficiently smooth to allow cells, compounds and particulate matter in the chamber to flow past the surface without adhering thereto or diffusing therein.

15. The method of claim 1 wherein said nutrient-containing fluid is serum-free.

16. The method of claim 1 wherein said nutrient-containing fluid is free of proteinaceous growth factors.

17. The method of claim 1 wherein said nutrient-containing fluid is conditioned by cell growth so that it contains proteinaceous growth factors.

18. The method of claim 17 wherein the level of proteinaceous growth factors in the fluid is enhanced by recycling said nutrient-containing fluid through said chamber while concurrently removing dividing cells from the chamber.

19. The method of claim 1 wherein said nutrient-containing fluid is caused to flow through said chamber at a flow rate that is sufficient to ensure that the oxygen saturation of the fluid is not greater than 20% at the inlet while remaining greater than 0% at the outlet relative to the solubility of oxygen in said fluid at equilibrium with air at 37° C. and 1 atm pressure.

20. The method of claim 19 wherein the flow rate is between 0.1 ml/hr and 8 ml/hr.

21. A method of making a bioreactor for the expansion and harvesting of a predetermined population of cells, said method comprising:
   (a) providing a chamber having an inlet, an outlet, and a passage for fluid flow from the inlet to the outlet, and, disposed in the chamber, a solid support capable of supporting a plurality of living cells adhered thereto, wherein said support comprises a plurality of binding sites with specific affinity for said predetermined population of cells;
   (b) causing fluid containing a plurality of cells of said cell population to flow through said chamber, at a rate selected so that a portion of said cells bind to said binding sites while unwanted cells are removed; and (c) freezing said chamber to preserve said cells in a potentially viable state.

22. A method of preserving and expanding a predetermined cell population comprising the steps of:

(a) providing a chamber having an inlet, an outlet, and a passage for fluid flow from the inlet to the outlet, and, disposed in the chamber, a solid support capable of supporting plurality of living cells adhered thereto, wherein said support comprises a plurality of binding sites with specific affinity for said predetermined population of cells;

(b) causing fluid containing a plurality of cells of said cell population to flow through said chamber, so that a portion of said cells bind to said binding sites; and (c) freezing said chamber to preserve said cells in potentially viable state;

(d) thawing said chamber;

(e) causing fluid containing nutrients to flow through said chamber to cause said bound cells to divide; and (f) continuously harvesting cells of said predetermined population as they exit said chamber with said fluid.

23. A method of obtaining a desired population of cells comprising:

(a) providing a sample containing a first population of cells which cells are the progenitor to the desired population of cells;

(b) passing a portion of the sample through a chamber containing a solid support capable of supporting a plurality of living cells adhered thereto, wherein said support comprises a plurality of binding sites with specific affinity for said first population of cells so that a portion of said cells bind to said binding sites;

(c) causing fluid containing nutrients to flow through said chamber at a rate selected to cause said bound cells to proliferate, differentiating to form said desired population of cells, and said desired population of cells to be released from the solid support; and (d) continuously harvesting said desired population of cells as they are released from the solid support.

24. A method of obtaining a desired population of cells comprising:

(a) providing a sample containing relatively undifferentiated cells;

(b) passing a portion of the sample through a chamber containing a solid support capable of supporting a plurality of living cells adhered thereto, wherein said support comprises a plurality of binding sites with specific affinity for said relatively undifferentiated cells so that a portion of said cells bind to said binding sites;

(c) causing fluid containing nutrients to flow through said chamber at a rate selected to cause said bound cells to proliferate and said desired population of cells to be released from the solid support, said fluid containing one or more growth factors selected to cause said cells to differentiate to form the desired population of cells;

(d) continuously harvesting said desired population of cells as they exit said chamber with said fluid.

25. The method of claim 1 wherein said nutrient-containing fluid contains exogenous proteinaceous growth factors.

26. The method of claim 1 wherein said cells of said predetermined population are continuously harvested as they exit said chamber.

* * * * *